US006194218B1

(12) United States Patent
Rieders et al.

(10) Patent No.: US 6,194,218 B1
(45) Date of Patent: Feb. 27, 2001

(54) BLOOD METHEMOGLOBIN ANALYSIS

(75) Inventors: Fredric Rieders, Rushland; Anthony J. Macherone, Philadelphia, both of PA (US)

(73) Assignee: The Fredric Rieders Family Renaissance Foundation, Willow Grove, PA (US)

( * ) Notice: Subject to any disclaimer, the term of this patent is extended or adjusted under 35 U.S.C. 154(b) by 0 days.

(21) Appl. No.: 09/235,472

(22) Filed: Jan. 22, 1999

(51) Int. Cl.$^7$ .................................................. G01N 33/72
(52) U.S. Cl. ............................. 436/66; 436/8; 436/17; 436/18; 436/164; 436/166; 436/176; 252/408.1
(58) Field of Search ............................. 436/8, 15, 17, 436/18, 63, 66, 164, 166, 176; 252/408.1; 422/82.05, 82.09, 99, 102; 435/2

(56) References Cited

U.S. PATENT DOCUMENTS

| | | | |
|---|---|---|---|
| 4,013,417 | * 3/1977 | Raffaele | 422/67 |
| 4,436,820 | * 3/1984 | Reiter | 436/67 |
| 5,051,353 | 9/1991 | Stratton et al. | 435/2 |
| 5,352,773 | 10/1994 | Kandler et al. | 530/385 |
| 5,476,764 | * 12/1995 | Bitensky | 435/2 |
| 5,692,503 | 12/1997 | Kuenstner | 128/633 |
| 5,858,794 | * 1/1999 | Malin | 436/66 |
| 5,961,469 | * 10/1999 | Roizen et al. | 600/531 |

FOREIGN PATENT DOCUMENTS

WO 97/39027    10/1997 (WO) .

OTHER PUBLICATIONS

Sakata et al. *Clinical Chemistry*, vol. 28, No. 3, pp. 508–511, 1982.*

Rossi–Bernardi et al. *Clinical Chemistry*, vol. 23, No. 7, pp. 1215–1225, 1977.*

Siek et al., "Determination of Carboxyhemoglobin in the Presence of Other Blood Hemoglobin Pigments by Visible Spectrophotometry", *J. Forensic Sci.*, Jan. 1984, p. 39–54.

Gordon C. Mills and Harvey P. Randall, "Hemoglobin Catabolism—II. The Protection of Hemoglobin From Oxidative Breakdown in the Intact Erythrocyte", *J. Biol. Chem.*, 232:589–598 (1958).

* cited by examiner

*Primary Examiner*—Maureen M. Wallenhorst
(74) *Attorney, Agent, or Firm*—Seidel, Gonda, Lavorgna & Monaco, PC

(57) ABSTRACT

Blood samples are stabilized for methemoglobin determination with a buffer composition containing (a) carbon monoxide-containing water; (b) sodium tetraborate or potassium tetraborate; and (c) KCN or NaCN. The buffer composition preferably may also have an erythrocytolysis agent. The buffer fixes the valence state of heme iron at a concentration representative of the blood at the time of collection, and maintains that fixed state for an extended period of time preventing further methemoglobin formation. The buffer also prevents reduction of existing target analyte, i.e., methemoglobin (ferric hemoglobin, $Fe^{3+}$ hemoglobin) to normal reduced hemoglobin (ferrous hemoglobin, $Fe^{2+}$ hemoglobin).

27 Claims, No Drawings

BLOOD METHEMOGLOBIN ANALYSIS

FIELD OF THE INVENTION

The invention relates to the field of blood analysis, specifically the testing of blood for methemoglobin content.

BACKGROUND OF THE INVENTION

Normally, the hemoglobin in circulating blood is usually more than 99% in the ferrous ($Fe^{2+}$) form. The ferrous form transports oxygen. Another form of hemoglobin, known as methemoglobin, contains the ferric ion ($Fe^{3+}$). Methemoglobin is unable to transport oxygen. In healthy individuals, the methemoglobin concentration in circulating blood is usually less than one percent. The iron in hemoglobin is kept in the ferrous valence state by the activity of a special methemoglobin reductase system. See Metzler, *Biochemistry*, Academic Press, New York, N.Y., 1997, pp. 564–565.

Methemoglobin is monitored to evaluate biological exposure to biotoxins and possible carcinogenic compounds which contain primary aromatic amino-, nitro-, nitroso-, azo- and/or certain phenolic moieties. These residues have been directly correlated to methemoglobin production both in vivo and in vitro. An elevated methemoglobin concentration can be indicative of exposure to these and/or other toxicants.

The normal methemoglobin concentration is less than 1% in normal, living persons. Shortly after blood is drawn from a living person, or after a person dies, the methemoglobin enzymatic reduction systems become disrupted and the hemoglobin iron starts moving towards a new equilibrium between the ferrous and the ferric state, i.e., from normal $Fe^{2+}$ hemoglobin toward $Fe^{3+}$ methemoglobin. In less than one hour after blood collection, the methemoglobin concentration can become spontaneously elevated to a level which is above the biological exposure limit of 1.5%, resulting in an erroneous interpretation of excessive toxicant exposure. In forensic cases, spontaneous bacterial or other thanatologic causes can not only produce apparently "toxic" levels of methemoglobin, but can also result in lowering causally significant levels of methemoglobin, thus rendering those levels misinterpretable.

The ability to accurately measure methemoglobin is presently limited to a narrow time window after sample collection via venipuncture or other collection methods, due to the spontaneous oxidation of hemoglobin to methemoglobin. What is needed is a quantitative methemoglobin analysis method wherein the time from blood collection to analysis may be extended without the risk of spontaneous methemoglobin production in the blood sample, which would otherwise undesirably increase the actual methemoglobin concentration present at the time of collection.

ABBREVIATIONS AND DEFINITION

By "hemoglobin" is meant the oxygen-carrying heme protein found in red blood cells consisting of two pairs of polypeptide chains and an iron-containing heme group. Unless indicated otherwise, "hemoglobin" shall mean normal hemoglobin, that is, the form of the protein which contains iron in the ferrous, that is, the $Fe^{2+}$, valence state.

By "methemoglobin" is meant the form of hemoglobin in which the contained iron is oxidized to the ferric state, that is, the $Fe^{3+}$, valence state.

By "oxyhemoglobin" is meant hemoglobin which contains bound oxygen, reversible bound to the iron in the heme group.

By "carboxyhemoglobin" is meant hemoglobin which contains bound carbon monoxide in lieu of oxygen. Carboxyhemoglobin may be generated by contacting hemoglobin with carbon monoxide.

By "cyanmethemoglobin" is meant methemoglobin which contains bound cyanide ions.

By "deoxyhemoglobin" is meant hemoglobin which does not contain bound oxygen. It is also known as "reduced hemoglobin".

By "erythrocytolysis agent" is meant an agent capable of lysing erythrocytes.

By "total hemoglobin", unless indicated otherwise, is meant the total of all forms of hemoglobin in a blood sample, comprising all of the above forms, and any other hemoglobin forms which may be present in a sample.

By "substantially convert" with respect to the conversion of one hemoglobin form present in a sample to another hemoglobin form is meant that at least about 90% of the initial form in the sample is converted to the other form. The degree of conversion is more preferably at least about 95%, most preferably at least about 99%.

By "fully oxygenated blood" is meant whole blood which has been purged with oxygen to the extent that essentially all of the hemoglobin contained therein is converted to oxyhemoglobin.

SUMMARY OF THE INVENTION

According to the present invention, a buffer composition is provided for stabilizing blood samples for methemoglobin determination. The buffer composition comprises:

(a) carbon monoxide-containing water;

(b) a tetraborate salt selected from the group consisting of sodium tetraborate, potassium tetraborate and combinations thereof; and (c) a cyanide compound selected from the group consisting of KCN, NaCN and combinations thereof. The buffer composition is added to a blood sample comprising lysed erythrocytes. Lysis releases the hemoglobin contained in the erythrocytes for analysis according to the present invention.

According to another embodiment of the invention, a method for preparing a buffer composition for stabilizing blood samples for methemoglobin determination is provided comprising dissolving in carbon monoxide-containing water the aforesaid tetraborate salt and cyanide compound. The carbon monoxide-containing water is preferably carbon monoxide-saturated water.

According to another embodiment, the invention comprises, in combination, a resealable spectrophotometer cuvette suitable for conducting spectrophotometric analysis over the wavelength range 500 nm to 650 nm, and a volume of the buffer composition contained in the cuvette.

According to another embodiment of the invention, a buffered blood preparation is provided comprising a blood sample and an amount of the buffer composition sufficient to substantially convert methemoglobin in the blood sample to cyanmethemoglobin. The solution contains a tetraborate salt selected from the group consisting of sodium tetraborate, potassium tetraborate and combinations thereof.

In yet another embodiment, the invention is a method of stabilizing blood for determination of methemoglobin content. The blood is treated with a carbon monoxide-saturated water solution providing cyanide ions in an amount sufficient to substantially convert methemoglobin in the blood sample to cyanmethemoglobin.

In another embodiment, the invention is a method for determining the percent methemoglobin content of a blood sample comprising:
  (a) substantially converting oxyhemoglobin and deoxyhemoglobin in the sample to carboxyhemoglobin, and substantially converting methemoglobin in the sample to cyanmethemoglobin;
  (b) measuring the spectrophotometric absorbance of the sample at wavelengths 528.3 nm ($A_{528.3}$) and 557.8 nm ($A_{557.8}$);
  (c) determining the amount of total hemoglobin in the sample; and
  (d) computing the percent methemoglobin according to the relationship:

$$\text{PercentMethemoglobin} = \left(\frac{A_{528.3} - A_{557.8}}{\text{TotalHemoglobin}}\right)(1000)$$

Oxyhemoglobin and deoxyhemoglobin in the blood sample are substantially converted to carboxyhemoglobin, and methemoglobin in the sample is substantially converted to cyanmethemoglobin. This may be achieved by dissolving the sample in a carbon monoxide-containing water buffer solution providing cyanide ions in an amount sufficient to substantially convert the methemoglobin in the blood sample to cyanmethemoglobin.

These and other embodiments of the invention are apparent from consideration of the following detailed description.

DETAILED DESCRIPTION OF THE INVENTION

According to the present invention, the level of methemoglobin is quickly and easily determined in a blood sample by mixing with a novel buffer composition which stabilizes the relative concentrations of ferrous ($Fe^{2+}$) and ferric ($Fe^{3+}$) hemoglobin forms, and prevents spontaneous generation or reduction of methemoglobin in the sample. The buffer contains carbon monoxide-containing water, that is, water which contains dissolved carbon monoxide. The buffer provides carbon monoxide to complex existing $Fe^{2+}$ hemoglobin, and cyanide ions to complex $Fe^{3+}$ hemoglobin. The buffer serves to fix the valence state of the iron in heme at a concentration which is representative of the system in a blood sample at the time of collection, and maintain that fixed state for an extended period of time. The buffer maintains the valence state of iron present at the time of blood collection for several days and inhibits further methemoglobin formation.

The buffer composition, which will typically take the form of a solution, comprises carbon monoxide-containing water, sodium tetraborate or potassium tetraborate, potassium cyanide or sodium cyanide. The tetraborate and cyanide compounds are dissolved in the carbon monoxide-containing water. Once the blood sample is introduced to the solution, oxyhemoglobin, the primary hemoglobin derivative in normal, circulating blood, and deoxyhemoglobin are instantaneously converted to carboxyhemoglobin by the presence of an excess of carbon monoxide in the buffer. Any methemoglobin present quickly reacts with the cyanide anion to form the stable cyanmethemoglobin complex. Carboxyhemoglobin initially present in the sample is unaffected by the buffer. Thus, the resulting system consists of two hemoglobin components: carboxyhemoglobin and cyanmethemoglobin. The methemoglobin present in the sample at the time of collection will equal the molar concentration of the cyanmethemoglobin, and is proportional to the absorbance difference at the isobestic points of cyanmethemoglobin and carboxyhemoglobin upon spectrophotometric analysis. The isobestic points of cyanmethemoglobin and carboxyhemoglobin are the two points at which their absorption spectra cross over. These points occur at 528.3 nm and 557.8 nm.

Hemoglobin will become denatured at extremes of pH. If the solution pH is too high, a denatured form of hemoglobin known as alkaline hematin will form. Conversely, if the solution pH is too low, the denatured hemoglobin form known as acidic hematin will result. The presence of these hematin forms is recognizable upon spectrophotometry. See Siek and Rieders, *J. For. Sci.*, 29(1):39–54(1984). To avoid the denaturation of hemoglobin and the generation of the hematins, the solution pH should be in the range of from about 6 to about 9.5, preferably in the range of from about 6.5 to about 9.0. Most preferably, the solution pH is about 8.5. The buffer composition maintains the blood sample at the latter pH for hemoglobin analysis, and thus prevents hemoglobin denaturation.

The blood sample comprises lysed erythrocytes. Lysis is required to release the hemoglobin for analysis. The erythrocytes may be lysed by any of the various erythrocytolysis agents known to those skilled in the art.

According to a preferred embodiment of the invention, the buffer composition contains an erythrocytolysis agent. This permits the buffer composition-to be used directly on whole blood immediately following drawing, without first subjecting the sample to erythrocytolysis to liberate the hemoglobin species contained in the cells. Erythrocytolysis and the concomitant liberation of hemoglobin species into the buffer solution, along with the conversion of the liberated hemoglobin species to carboxyhemoglobin and cyanmethemoglobin, proceeds essentially simultaneously.

Upon addition of a blood sample to the buffer solution, which is conveniently contained in a disposable, re-sealable, spectrophotometric cuvette, there is no need for further sample preparation. Blood collection can be accomplished from either a finger or earlobe prick, as only 25 $\mu$l to 50 $\mu$l of blood are necessary for the assay. The volume of buffer for the assay is conveniently 2 ml, but other volumes may be utilized. The dilution of 25–50 $\mu$l of blood in 2 ml of buffer places the absorbance of the predominate spectral bands in a range of 0.7 to 1.5 absorbance units. This is well within the linear region for visible spectrophotometry.

Methemoglobin concentrations can be determined spectrophotometrically by placing the cuvette in the spectrophotometer, scanning from 500 nm to 650 nm and determining the absorbance at 528.3 nm and 557.8 nm (the isobestic points for cyanmethemoglobin and carboxyhemoglobin), and determining the maximum absorbance near 568.3 nm ($A_{max}$). The $A_{max}$ value is used to determine total hemoglobin, which requires a determination of the percent carboxyhemoglobin of the sample. The latter is based upon the absorbance difference at 529.3 nm and 583.0 nm. The wavelength "529.x" is determined from a reference sample during spectrophotometer calibration, as described later.

The time period between sample collection and spectrophotometric analysis can be conveniently increased without concern for spontaneous methemoglobin production, which would otherwise undesirably increase the actual methemoglobin concentration present at the time of collection. After analysis, the sample can be stored for several days or at 0° C. and re-evaluated for methemoglobin again, with no observed further methemoglobin production.

The aqueous buffer of the invention is based upon carbon monoxide-containing water, that is, water which contains dissolved carbon monoxide. The water should contain sufficient carbon monoxide to bind all of the hemoglobin in the sample which is convertible to carboxyhemoglobin. Such convertible hemoglobin comprises oxyhemoglobin and deoxyhemoglobin. An excess of carbon monoxide over the carbon monoxide binding capacity of the sample should therefore be provided. The carbon monoxide excess is preferably at least about two-fold, more preferably at least about five-fold, most preferably at least about ten-fold.

The carbon monoxide binding capacity of whole blood, assuming that whole blood contains 0.15 grams of hemoglobin per ml, is about 0.18 ml of carbon monoxide per ml of blood. According to a preferred embodiment of the invention, 2 ml of buffer is combined with a 25 $\mu$l whole blood sample for assay. The carbon monoxide capacity of 25 $\mu$l of whole blood is approximately 4.5 $\mu$l of carbon monoxide. The 2 ml volume of buffer formed from carbon monoxide-saturated water will contain 46 $\mu$l of carbon monoxide. This amount of carbon monoxide is approximately ten times the amount required to satisfy the carbon monoxide capacity of the 25 $\mu$l blood sample.

The carbon monoxide saturation point of water at room temperature is 23 $\mu$l of carbon monoxide per ml of water. It is possible that the carbon monoxide level of the carbon monoxide-containing water used to prepare the buffer of the present invention may be less than the saturation amount. Preferably, the level is at least about 20% of saturation, more preferably at least about 50% of saturation, most preferably at least about 99% of saturation. Water which has been substantially fully saturated with carbon monoxide is most preferred.

Carbon monoxide-saturated water may be prepared by generating carbon monoxide by the dehydration of formic acid upon treatment with sulfuric acid connected to a bubbler containing NaOH. See Gilliland and Blanchard, *Inorg. Synth.* 2:81–85 (1946), incorporated herein by reference. The exhaust of the bubbler is directed to a semi-sealed vessel containing de-ionized water for saturation with carbon monoxide. Saturation may be confirmed by adding 0.1 ml of whole blood to 2.0 ml of the water and measuring the percent of hemoglobin present as carboxyhemoglobin. A percent carboxyhemoglobin reading of at least 95% will confirm that the water is saturated with carbon monoxide.

In addition to dissolved carbon monoxide to complex existing $Fe^{2+}$ hemoglobin, the buffer solution contains a cyanide compound which provides cyanide ions to complex with methemoglobin, to form cyanmethemoglobin. The amount of cyanide compound should be sufficient to provide enough cyanide ions to quickly convert substantially all the methemoglobin in the sample to cyanmethemoglobin. The cyanide ions are provided by KCN or NaCN, with KCN being preferred. The buffer composition contains from about 1 to about 3 mg of the cyanide compound, per deciliter of volume of the carbon monoxide-containing water which forms the major portion of the buffer. More preferably, the cyanide compound concentration is from about 1.8 to about 2.2 mg per deciliter of the carbon monoxide-containing water.

The buffer solution further contains sodium tetraborate or potassium tetraborate, with sodium tetraborate being preferred. Sodium tetraborate serves to buffer the composition to pH 8.5, to ensure that the hemoglobin will not denature. The presence of the tetraborate serves to slow or completely stop the oxidation of hemoglobin to methemoglobin. In this regard, a 50-fold dilution of blood in a sodium tetraborate buffer, even without dissolved carbon monoxide or cyanide compound, was observed to resist formation of methemoglobin for 21 days following addition of 0.02 mg sodium nitrite per ml of tetraborate buffer. The same nitrite concentration in an identically prepared sample, with the exception of sodium tetraborate, resulted in 100% conversion of hemoglobin to methemoglobin in 5.8 hours.

The buffer composition advantageously contains from about 2.5 to about 3.5 grams of the tetraborate compound, per deciliter of volume of the carbon monoxide-containing water. More preferably, the tetraborate compound concentration is from about 1.8 to about 2.2 grams per deciliter of the carbon monoxide-containing water.

The buffer composition preferably contains an erythrocytolysis agent. Any agent capable of lysing erythrocytes under the assay conditions described herein may be utilized, provided it does not interfere with the conversion of hemoglobin to carboxyhemoglobin, or the conversion of methemoglobin to cyanmethemoglobin. Further, the erythrocytolysis agent should not interfere with the spectrophotometric analysis of the various hemoglobin forms. Thus, the erythrocytolysis agent should not absorb electromagnetic radiation over the wavelength range of 500 nm to 650 nm. Also, the agent should not denature hemoglobin, such as by causing the solution pH to depart from the 6–9.5 range. Preferably, the erythrocytolysis agent will not cause the solution pH to depart from the range of 6.5 to 9.

Also, the erythrocytolysis agent should act to reduce the turbidity of the solution. Turbidity causes the scattering of light, and results in instrumental variations from Beer's Law in the spectrophotometric analysis of hemoglobin according to the present invention. Turbidity arises from the presence of large particles. An ideal erythrocytolysis agent will be capable of substantially dissolving erythrocytes to produce a substantially clear solution (although the solution may be colored). An ideal erythrocytolysis agent will also have surfactant properties, to reduce the solution surface tension and thus inhibit agglutination of small particles into larger particles.

The following evaluation may be utilized in order to determine whether a given chemical agent is suitable as an erythrocytolysis agent for use in the practice of the present invention, with respect to the desired properties of erythrocyte lysing ability, inhibition of turbidity (by inhibition of particle agglutination) and noninterference with spectrophotometry.

First, the spectrophotometric absorbance of the candidate agent may be found in the literature or empirically determined by visible spectrophotometry. The agent should not absorb over the wavelength 500 nm to 650 nm.

Second, the erythrocytolysis ability of the candidate agent may be determined via microscopy by preparing a dilute solution of the agent and adding a fixed volume of whole blood. An aliquot of the resulting solution can be obtained at several time intervals to determine the extent and the amount of time required to completely rupture the erythrocytes. Ideally, the time frame would be less than five minutes, more preferably less than three minutes, most preferably less than one minute.

Third, the extent to which the agent provides a clear, that is, non-turbid solution under the conditions of the herein hemoglobin analysis can be determined empirically by preparing buffer solutions as described herein containing the candidate erythrocytolysis agent. An initial baseline absorbance of the candidate agent is determined over the wavelength region 600 nm to 650 nm. Absorbance in this range is due to the general turbidity of the solution and the inherent absorptivity of the chromophore moieties in the structure of the candidate agent. Next, the same reading is taken after addition of a blood sample, following a brief incubation period in which the candidate erythrocytolysis agent is allowed to lyse the erythrocytes in the blood sample (e.g., 5 minutes). The absorbance over the wavelength 600 to 650 nm should not increase more than 0.2 absorbance units, more preferably not more than 0.1 absorbance units, most preferably not more than 0.05 absorbance units. If the absorbance increase is more than 0.2 absorbance units, the candidate erythrocytolysis agent should be rejected.

In one preferred embodiment, the erythrocytolysis agent is able not only to hemolyze the erythrocytes in the blood sample, but also serves to de-activate methemoglobin reductase and other endogenous iron reduction mechanisms in the sample.

One preferred agent with the aforementioned properties is octylphenoxy polyethoxy ethanol, available as Triton® X-100 from Rohm and Haas Co., Philadelphia, Pa. The presence of the cyanide compound and octylphenoxy polyethoxy ethanol greatly reduce the chance of methemoglobin reduction to oxyhemoglobin or deoxyhemoglobin, which would unintentionally and unpredictably lower the methemoglobin concentration from that of the original sample. Octylphenoxy polyethoxy ethanol is a nonionic surfactant having an HLB of 13.5. Other suitable solvents will be apparent to those skilled in the art.

The erythrocytolysis agent is present in an amount sufficient to provide rapid lysis of erythrocytes in the blood sample. From about 1 to about 100 microliters of the agent, per deciliter of the carbon monoxide-containing water is generally acceptable. More preferred is an amount of erythrocytolysis agent in the range of from about 40 to about 100 microliters, most preferably from about 45 to about 55 microliters, per deciliter of carbon monoxide-containing water.

The buffer composition is conveniently prepared by adding a portion of the total final volume of carbon monoxide-containing water to finely ground tetraborate compound, which is then allowed to dissolve with minimal shaking. Next, the cyanide compound and erythrocytolysis agent are added, followed by the remainder of the carbon monoxide-containing water. The order of addition of components is not critical. The solution should be kept tightly sealed until use.

Ferrous hemoglobin has an affinity for carbon monoxide which is over 200 times greater than its affinity for oxygen. Thus, carbon monoxide readily displaces oxygen in oxyhemoglobin to form stable carboxyhemoglobin. There is no apparent tendency for oxygen in dilute aqueous solutions to displace the carbon monoxide in carboxyhemoglobin. However, carbon monoxide is lost to ambient air when blood samples containing carboxyhemoglobin are exposed to air. The buffer solution is thus advantageously dispensed into resealable spectrophotometry cuvettes suitable for spectrophotometric analysis over the visible light band. The buffer-containing cuvette should be resealable so that it may be opened for insertion of the blood sample, but otherwise remain sealed until analysis. This will minimize the loss of carboxyhemoglobin in the sample as carbon monoxide is lost to the ambient air. The loss of carboxyhemoglobin opens the potential for the iron to oxidize to the trivalent state, thus perturbing the actual methemoglobin concentration.

A resealable cuvette is characterized by a resealable closure means such as a screw top, a snap-tight cap, a stopper, or a self-sealing septum pierceable by the needle of a syringe, or other sealing arrangements known to those skilled in the art which provide an essentially air tight seal.

The sample for analysis contains erythrocytes. Typically, the sample will comprise whole blood, or fraction thereof containing erythrocytes.

The buffer composition is utilized as follows. A convenient amount of blood, preferably from about 25 to about 50 microliters, is collected by either finger or earlobe prick. The sample is placed directly into the resealable cuvette containing the buffer solution by the phlebotomist at the place of collection. There is no need for STAT transport as the buffer solution will stabilize the ferric/ferrous ratio in the sample for up to one month at ambient temperatures. However, the sample should be analyzed within one week in any event.

The sample in the cuvette is then placed in a calibrated, background-corrected spectrophotometer and scanned at 528.3 nm, 529.3 nm, 557.8 nm and 583.0 nm. The maximum absorbance near 568.3 nm is also determined ($A_{max}$). The percent methemoglobin is determined as follows:

$$\text{PercentMethemoglobin} = \left(\frac{A_{528.3} - A_{557.8}}{\text{TotalHemoglobin}}\right)(1000) \qquad \text{Eq. 1}$$

wherein:

$A_{528.3}$=the absorbance at 528.3 nm=the absorbance at 589.3 nm;

$A_{557.8}$=the absorbance at 557.8 nm; and $$\text{TotalHemoglobin} = \left(\frac{A_{max}}{E*}\right)(\text{Dilution}) \qquad \text{Eq. 2}$$

wherein:

$$\text{Dilution} = \left(\frac{\text{volume}_{buffer} + \text{volume}_{blood}}{\text{volume}_{blood}}\right) \qquad \text{Eq. 3}$$

and E* is the composite absorptivity for total hemoglobin at a given carboxyhemoglobin blood content.

E* is a variable based upon the percent carboxyhemoglobin in the sample. It has a value ranging from 8.3 to 9.2. E* for a given percent carboxyhemoglobin may be determined from the following table taken from Siek and Rieders, *J. For. Sci.*, 29(1):39–54(1984), the entire disclosure of which is incorporated herein by reference:

TABLE 1

Composite absorptivity E* for total hemoglobin at various carboxyhemoglobin (HbCO) contents of blood

| % HbCO | E* | % HbCO | E* |
|---|---|---|---|
| 0 | 9.2 | 40 | 8.4 |
| 5 | 9.1 | 50 | 8.3 |
| 10 | 9.0 | 60 | 8.4 |
| 20 | 8.8 | 75 | 8.5 |
| 30 | 8.6 | 100 | 8.6 |

The percent carboxyhemoglobin for determination of E* is calculated from the equation:

$$\text{PercentCarboxyhemoglobin} = \left(\frac{A_{529.x} - A_{583.0}}{A_{max}}\right)(235) \quad \text{Eq. 4}$$

wherein:

$A_{529.x}$=the absorbance at 529.x nm; and $A_{583.0}$=the absorbance at 583.0 nm.

The wavelength "529.x" is determined as follows from a reference sample during spectrophotometer calibration. Whole blood is purged with oxygen to convert essentially 100% of the hemoglobin in the blood to oxyhemoglobin ("fully oxygenated blood"). The fully oxygenated blood is added to a solution of 0.4% v/v ammonium hydroxide in the volume-to-volume of 1 part blood to 100 parts ammonium hydroxide solution. This is the dilution at which absorbance of the oxygenated blood at 576 nm is about 1. The absorbance at 583 nm is determined and then the absorbance near 529 nm, 529.1 nm, 529.2 nm, etc. is determined. The wavelength "529.x" is selected as the wavelength at which the absorbance is identical to the absorbance of the sample at 583 nm, i.e. the wavelength 529.x such that $A_{529.x} - A_{583}$ is zero. The determined value, 529.x, is then used in the above determination of percent the carboxyhemoglobin. Typically, the value of 529.x will fall at or near 529.3 nm. Instruments should be calibrated in this manner at least three times per year.

The percent carboxyhemoglobin should be greater than 91%. A lower value suggests that the sample has been left standing too long to ensure an accurate determination of methemoglobin.

The total hemoglobin should be in the range of from 12 to 17 g/dl. A value outside this range suggests that the hemoglobin in the sample has been denatured.

The mass of iron in milligrams may also be determined from the collected data: wherein:

$$\text{MassFemg} = (\text{Hemoglobintotal})(3.4) \quad \text{Eq. 5}$$

The practice of the invention is illustrated by the following nonlimiting examples.

EXAMPLE 1

Preparation of Buffer Solution

A solution containing CO-saturated water (0.023 ml CO per ml water at 20° C.), 3% wt/v sodium tetraborate, 20 μg/ml KCN and 0.05% octylphenoxy polyethoxy ethanol (Triton® X-100) was prepared as follows.

CO was generated by the dehydration of formic acid. Formic acid was treated with sulfuric acid in a 50 ml round bottom flask connected to a bubbler containing approximately 20 ml of 6N NaOH. The exhaust of the bubbler was plumbed to a semi-sealed vessel containing about 125 ml of de-ionized water. The CO which was generated was allowed to purge through the water until the dehydration of the formic acid became sluggish. This process was repeated twice, until the water became saturated with CO.

Approximately 80 ml of the CO-saturated water was added to a 100 ml volumetric flask containing 3 grams of finely divided ground sodium tetraborate ($Na_2B_4O_7$). The sodium tetraborate was allowed to dissolve with minimal shaking of the flask. Then 2.0 ml of a 1.0 mg/ml stock solution of KCN along with 50 μl of Triton® X-100 detergent was added to the flask. The flask was then filled to the fill line with CO-saturated water. The solution appeared to be stable for at least one week in a tightly sealed vessel at 0° C.

EXAMPLE 2

Sample Analysis

Spectrophotometer Calibration

Whole blood was purged with oxygen to ensure that 100% of the hemoglobin was in the form of oxyhemoglobin. The blood was then added to a solution of 0.4% v/v ammonium hydroxide at a dilution of approximately 100:1 (or where the absorbance at 576 nm is about 1.0). The absorbance at 583 nm was determined and then the absorbance near 529 nm, 529.1 nm, 529.2 nm, etc. was determined such that the difference of $A_{529.x} - A_{583}$ was zero. The determined value, 529.3, was then used for the hemoglobin determinations below.

Sample Analysis

Two ml of the buffer solution of Example 1 was placed into a disposable 2 ml semi-micro cuvette. The cuvette was manufactured by attaching the top threaded portion of a glass 13 mm×100 mm test tube to 2 ml semi-micro cuvette with epoxy. 25 microliters of whole blood was added to the cuvette and the cuvette was then sealed and gently inverted to hemolyze and evenly distribute the blood in the solution. The cuvette was placed into the calibrated spectrophotometer and the solution scanned from 500 nm to 650 nm. The absorbance at 528.3 nm, 529.3 nm, 557.8 nm, 583.0 nm, and the maximum absorbance near 568.3 nm, was determined for the calculation of percent methemoglobin. The percent methemoglobin was determined from Equations 1–4, above.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

What is claimed is:

1. A buffer composition for stabilizing blood samples for methemoglobin determination comprising:
   (a) carbon monoxide-containing water;
   (b) a tetraborate salt selected from the group consisting of sodium tetraborate, potassium tetraborate and combinations thereof; and
   (c) a cyanide compound selected from the group consisting of KCN, NaCN and combinations thereof.

2. The composition according to claim 1 comprising, per deciliter of carbon monoxide-containing water, from about 2.5 to about 3.5 grams of the tetraborate salt and from about 1 to about 3 mg of the cyanide compound.

3. The composition according to claim 2 comprising, per deciliter of carbon monoxide-containing water, from about 2.9 to about 3.1 grams of the tetraborate salt and from about 1.8 to about 2.2 mg of the cyanide compound.

4. The composition according to claim 1 further comprising an erythrocytolysis agent.

5. The composition according to claim 4 comprising, per deciliter of carbon monoxide-containing water, from about 40 to about 100 microliters of the erythrocytolysis agent.

6. A combination comprising a resealable spectrophotometer cuvette suitable for conducting spectrophotometric analysis over the wavelength range 500 nm to 650 nm and a volume of the buffer composition of claim 4 contained in said cuvette.

7. A buffered blood preparation comprising a blood sample and an amount of a buffer composition according to claim 4 sufficient to substantially convert methemoglobin in the blood sample to cyanmethemoglobin.

8. The composition according to claim 1 wherein the cyanide compound is KCN and the tetraborate salt is sodium tetraborate.

9. The composition according to claim 8 containing an erythrocytolysis agent which is octylphenoxy polyethoxy ethanol.

10. The composition according to claim 9 wherein the carbon monoxide-containing water is saturated with carbon monoxide.

11. The composition according to claim 10 comprising, per deciliter of carbon monoxide-saturated water, from about 2.5 to about 3.5 grams sodium tetraborate, from about 1 to about 3 mg KCN, and from about 0.002 to about 0.023 ml octylphenoxy polyethoxy ethanol.

12. A combination comprising a resealable spectrophotometer cuvette suitable for conducting spectrophotometric analysis over the wavelength range 500 nm to 650 nm and a volume of the buffer composition of claim 11 contained in said cuvette.

13. A buffered blood preparation comprising a blood sample and an amount of a buffer composition according to claim 11 sufficient to substantially convert methemoglobin in the blood sample to cyanmethemoglobin.

14. A combination comprising a resealable spectrophotometer cuvette suitable for conducting spectrophotometric analysis over the wavelength range 500 nm to 650 nm and a volume of the buffer composition of claim 8 contained in said cuvette.

15. A buffered blood preparation comprising a blood sample and an amount of a buffer composition according to claim 8 sufficient to substantially convert methemoglobin in the blood sample to cyanmethemoglobin.

16. A combination comprising a resealable spectrophotometer cuvette suitable for conducting spectrophotometric analysis over the wavelength range 500 nm to 650 nm and a volume of the buffer composition of claim 1 contained in said cuvette.

17. A buffered blood preparation comprising a blood sample and an amount of a buffer composition according to claim 1 sufficient to substantially convert methemoglobin in the blood sample to cyanmethemoglobin.

18. A method for preparing a buffer composition for stabilizing blood samples for methemoglobin determination comprising dissolving in carbon monoxide-containing water:
   (a) a tetraborate salt selected from the group consisting of sodium tetraborate, potassium tetraborate and combinations thereof; and
   (b) a cyanide compound selected from the group consisting of KCN, NaCN and combinations thereof.

19. The method according to claim 18 comprising dissolving in the carbon monoxide-containing water, per deciliter of said water, from about 2.5 to about 3.5 grams of the tetraborate salt and from about 1 to about 3 mg of the cyanide compound.

20. The method according to claim 18 wherein the carbon monoxide-containing water is carbon monoxide-saturated water.

21. The method according to claim 18 further comprising dissolving an erythrocytolysis agent in the carbon monoxide-containing water.

22. The method according to claim 21 wherein the erythrocytolysis agent is octylphenoxy polyethoxy ethanol.

23. A method of stabilizing blood for determination of methemoglobin content comprising treating said blood with a carbon monoxide-saturated water solution providing cyanide ions in an amount sufficient to substantially convert any methemoglobin in the blood to cyanmethemoglobin, said solution further containing a tetraborate salt selected from the group consisting of sodium tetraborate, potassium tetraborate and combinations thereof.

24. The method of claim 23 wherein said cyanide ions are provided by a cyanide compound selected from the group consisting of KCN, NaCN and combinations thereof.

25. The method of claim 24 wherein the solution comprises, per deciliter of carbon monoxide-saturated water, from about 2.5 to about 3.5 grams of the tetraborate salt and from about 1 to about 3 mg of the cyanide compound.

26. The method of claim 25 wherein the solution further comprises an erythrocytolysis agent.

27. The method of claim 26 wherein the cyanide compound is KCN, the tetraborate salt is sodium tetraborate, and the erythrocytolysis agent is octylphenoxy polyethoxy ethanol.

* * * * *